United States Patent [19]

Sugier et al.

[11] Patent Number: 4,915,176

[45] Date of Patent: Apr. 10, 1990

[54] METHOD OF TRANSPORTING A HYDRATE FORMING FLUID

[75] Inventors: André Sugier; Paul Bourgmayer, both of Rueil Malmaison; Emmanuel Behar, Cergy; Edouard Freund, Rueil Malmaison, all of France

[73] Assignee: Institut Francais du Petrole, Rueil Malmaison, France

[21] Appl. No.: 288,985

[22] Filed: Dec. 23, 1988

[30] Foreign Application Priority Data

Dec. 30, 1987 [FR] France .................... 87 18435

[51] Int. Cl.⁴ .................... E21B 37/06; E21B 41/02; E21B 43/01; F17D 1/14
[52] U.S. Cl. .................... 166/371; 166/902; 137/13; 252/8.551
[58] Field of Search ............ 166/310, 370, 371, 902; 137/13; 252/8.551, 8.552

[56] References Cited

U.S. PATENT DOCUMENTS

| | | | |
|---|---|---|---|
| 3,348,614 | 10/1967 | Sinclair et al. | 166/310 |
| 4,132,535 | 1/1979 | Rivers, Jr. et al. | 137/13 X |
| 4,256,282 | 3/1981 | Goldschlid et al. | 166/310 X |
| 4,625,803 | 12/1986 | Walhaug et al. | 166/310 |
| 4,697,426 | 10/1987 | Knowles, Jr. | 166/370 X |
| 4,702,758 | 10/1987 | Geer | 166/370 X |

FOREIGN PATENT DOCUMENTS

| | | | |
|---|---|---|---|
| 612901 | 1/1961 | Canada | 166/310 |
| 644941 | 1/1979 | U.S.S.R. | 166/310 |
| 1275088 | 12/1986 | U.S.S.R. | 166/371 |
| 1314019 | 5/1987 | U.S.S.R. | 166/371 |
| 1339235 | 9/1987 | U.S.S.R. | 166/310 |

*Primary Examiner*—George A. Suchfield
*Attorney, Agent, or Firm*—Antonelli, Terry & Wands

[57] ABSTRACT

A method is provided for transporting in a duct a fluid comprising gas and water, and being under conditions where at least one hydrate is formed, the hydrates being formed from said gas and said water, wherein, before or during the formation of the hydrate or hydrates, an additive is injected into said fluid for reducing the tendency to agglomeration of the hydrate so as to obtain one or more hydrates in dispersed form, and said fluid is transported containing said hydrate or hydrates in dispersed form.

14 Claims, 2 Drawing Sheets

METHOD OF TRANSPORTING A HYDRATE FORMING FLUID

The invention relates to a method of transporting a fluid containing gas and water, the fluid being under conditions where at least one hydrate is formed. The gases, such as natural gas, petroleum gas or other gases, which form hydrates with water may comprise in particular methane, ethane, ethylene, propane, propene, n-butane, ibutane, $H_2$ and/or $CO_2$.

These hydrates are formed when the water is in the presence of the gas, either in the free state, or in the dissolved state in a liquid phase, such as a liquid hydrocarbon, and when the temperature reached by the mixture of water, gas and possibly liquid hydrocarbons, such as oil, becomes less than the thermodynamic temperature for the formation of hydrates, this temperature being given for a known composition of gases and when their pressure is fixed.

The formation of hydrates may be feared, particularly in the oil and gas industry, in which the conditions for the formation of hydrates may be present. In fact, to reduce the cost of crude oil and gas production, both from the investment and the working points of view, one approach, particularly for sea production, is to reduce even omit the treatments applied to the crude or to the gas to be transported from the production field to the coast and in particular to leave some or all of the water in the fluid to be transported. These offshore treatments are generally effected on a platform located at the surface near the field, so that the initially hot effluent may be processed before the thermodynamic conditions of hydrate formation are reached because of the cooling of the effluent with sea water.

However, as happens in practice, when the thermodynamic conditions required for the formation of hydrates are present, the agglomeration of the hydrates causes filling and blocking of the transport ducts by creating plugs which prevent any crude oil or gas from passing.

The formation of hydrate plugs may cause a shutdown of production and so considerable financial losses. In addition, bringing the installation back into service, especially if it is a question of production or sea transport, may be very long for the decomposition of the hydrates formed is very difficult to carry out. In fact, when the production of an underwater natural gas or oil and gas field comprising water reaches the surface of the sea bed, and is then transported at the bottom of the sea, it happens, through lowering of the temperature of the effluent produced, that the thermodynamic conditions are present for hydrates to form, agglomerate and block the ducts. The temperature at the bottom of the sea may for example be 3° or 4° C.

Conditions favorable to the formation of hydrates may also be present in the same way on land, for ducts which are not at all or not deeply buried in the earth, when for example the temperature of the ambient air is too cold.

To avoid such drawbacks, either inhibitors are added which lower the thermodynamic hydrate formation temperature, or the transport ducts are lagged, so as to prevent the temperature of the fluid transported reaching the temperature of formation of hydrates under operating conditions.

These two solutions are very expensive because, for the first one, the amount of formation inhibitors, the most widely used of which are methanol and ethylene glycol, may reach 10 to 20% of the water content and these inhibitors are difficult to recover completely; and for the second of these solutions, lagging of the duct is also very expensive.

It has been discovered that some amphiphilics added to the fluid, which up to now have not been used for this purpose, have excellent efficiency in lowering the hydrate formation temperature and/or modifying the mechanism of formation of such hydrates. This modification of the mechanism may particularly and advantageously be used for the transport of hydrate generating fluids.

The amphiphilic compounds are chemical compounds having a hydrophilic or polar part and an oleophile or lipophilic part.

In fact, instead of observing that the hydrates agglomerate with each other to form very solid blocks and plugs, or deposits in the appliances through which the hydrate generating fluid flows, it has been observed, throughout a wide temperature range, that such compounds disperse these hydrates in the fluid and then prevent their agglomeration.

When a mixture of gas, fluids and certain amphiphilic compounds are subjected to a temperature appreciably lower than the temperature at which hydrates begin to form, thickening of the fluid occurs without formation of blocks or plugs, such thickening being all the greater the lower the temperature. Such thickening of the fluid is due, on the one hand, to the increase in the viscosity of the fluid under the effect of the temperature and, on the other hand, to the presence of hydrate particles in dispersed form.

Dynamic tests using certain amphiphilic compounds have shown that the transport of fluid saturated or being saturated, with hydrates is possible.

Apart from this ability to disperse the hydrates which are formed in the fluid, the amphiphilic compounds observed may lower the temperature at which hydrates begin to form, more or less depending on their concentration, and reduce the cost of transporting fluids likely to form hydrates because of the low amounts of products used (generally less than 1% by weight with respect to the water) and for a moderate unitary cost thereof.

Such amphiphilic compounds, or more generally such additives used alone, in a mixture, or in the presence of other compounds (methanol, glycol) containing such compounds which are used in accordance with the invention for transporting a fluid generating or likely to generate gas hydrates are chosen, for example, from the non ionic amphiphilic compounds, the anionic amphiphilic compounds and the cationic amphiphilic compounds.

The non ionic amphiphilic compounds are characterized in that they comprise:

a hydrophilic part comprising either alkylene oxide, hydroxy or else alkylene amine groups, an oleophilic part comprising a hydrocarbon chain derived from an alcohol, a fatty acid, an alkylated derivative of phenol, or a polyolefin based for example on isobutene or butenes.

a bond between the hydrophilic part and the oleophilic part which may for example be an ether, ester or amide bridge; the bond may further be obtained by a nitrogen or sulphur atom.

Among the non ionic amphiphilic compounds may be mentioned the oxyethylated fatty alcohols, the alcoxylated alkylphenols, the oxyethylated and/or oxypropylated derivatives, sugar ethers, polyol esters, such as glycerol, polyethylene glycol, sorbitol or sorbitan, sugar esters, mono and diethanolamides, carboxylic acid amides, sulfonic acids or amino acids The anionic amphiphilic compounds are characterized in that they comprise one or more functional groups, ionizing in an aqueous solution to provide negative charged ions responsible for the surface activity. Such a functional group is an acid group salified by a metal or an amine. The acid may for example be carboxylic, sulfonic, sulfuric etc.

Among the anionic amphiphilic compounds may be mentioned:

carboxylates, such as metal soaps, alkaline soaps or organic soaps (such as N-acylaminoacids, N-acylsarcosinates, N-acylglutamates, N-acylpolypeptides),
   sulfonates such as alkylbenzenesulfonates, e.g. alcoxylated alkylbenzenesulfonates, paraffin sulfonates, olefin sulfonates, petroleum sulfonates, lignosulfonates or sulfosuccinic derivatives (such as sulfosuccinamates, hemisulfosuccinates, dialkylsulfosuccinates, such as sodium dioctylsulfosuccinate),
   sulfates, such as alkylsulfates, alkylethersulfates, and phosphates.

The cationic amphiphilic compounds are characterized in that they comprise one or more functional groups ionizing in an aqueous solution to provide positively charged ions responsible for the surface activity.

Among the cationic amphiphilic compounds may be mentioned alkylamine salts, such as alkylaminethers, quaternary ammonium salts, such as alkyltrimethylammonium derivatives, alkyltriethylammonium derivatives, alkyldimethylbenzylammonium derivatives, alcoxylated alkylamine derivatives, heterocyclic derivatives, such as pyridinium, imidazolinium, quinolinium, piperidinium or morpholinium derivatives.

Figure 1:
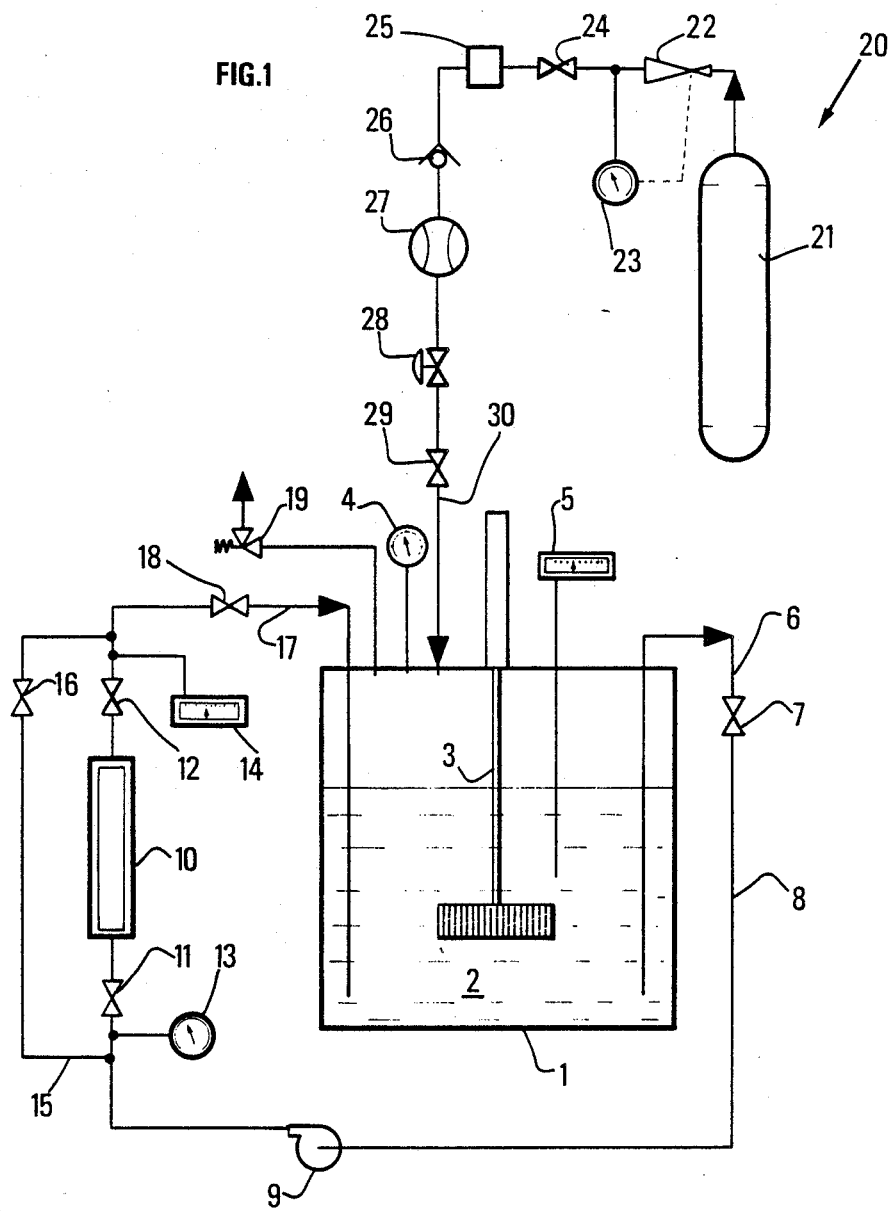
FIG. 1 is a schematic view of the apparatus for simulating the transport of hydrate-forming liquids and for observing the dispersing activity of additives on the hydrates.

In order to simulate the transport of hydrate forming fluids such as oil production effluents, and to observe the dispersing action of certain additives on the hydrates and for evaluating the efficiency of the additives, tests of hydrate formation from gas, condensate and water were carried out using an apparatus shown in FIG. 1.

The apparatus comprises a thermo-regulated reactor 1 of a volume of 2 liters in which a liquid 2 is placed, such as a condensate and water mixture, which is permanently stirred by an agitator 3 mounted at the end of a turbine. The gas supply for reactor 1 is regulated by a pressure gauge 4, the temperature of the reactor and of the circulation loop is controlled by means of thermostatic baths whose temperature is regulated by the temperature probe 5. A pipe 6 plunging on one side into liquid 2 supplies by its other side a circulation loop 8 which can be closed by valve 7.

In the circulation loop 8 is placed a pump 9 for causing the fluid and gas to flow. Loop 8 further comprises an observation chamber 10, which can be isolated by two valves 11 and 12 in which the formation of hydrates can be observed.

Upstream and downstream of this chamber are provided respectively a pressure indicator 13 and a temperature indicator 14. The apparatus comprises a shunt 15 across the observation chamber, this shunt being provided with a shut-off valve 16.

The fluid and the gas, having passed through the observation chamber 10 or shunt 15, are led back to reactor 1 through a return pipe 17. The circuit of the return pipe may be isolated by means of a valve 18. Reactor 1 further comprises a safety valve 19.

The gas supply for reactor 1 is provided by the circuit generally designated at 20 and which comprises, mounted one after the other, the following elements: a gas reservoir 21, a pressure reducer 22, a pressure gauge 23 with reference pressure controlling the pressure reducer 22, a closure valve 24, a filter 25, a non return valve 26, a flowmeter 27, an electronic valve 28 controlled by the pressure gauge 4 and providing the pressure reference inside the reactor by modification of the gas flow, a shut-off valve 29 and a supply pipe 30 penetrating into the reactor.

In one embodiment, the circulation loop 8 is ten meters long and is formed from a tube of about 19 mm(3/4") inner diameter. The circulating pump 9 provides flow rates up to 1 m/sec.

The formation of hydrates by reaction of the gas with the water results in a gas consumption which is determined by the flowmeter 27, and which is controlled by the electric valve 28 and the differential pressure sensor 23, so that the pressure is maintained constant in the circuit within 1/50th of a bar.

The experiment is carried out under a pressure of 7 MPa kept constant by a gas supply.

To determine the temperature at which the hydrates are formed, a rapid lowering of the temperature at the rate of 3° C. per hour is carried out from ambient temperature to 1° C.

Having then noted the temperature at which hydrates begin to form, which results in a consumption of gas, the temperature of the reactor and of the circulation loop is raised to 5° C. above this formation temperature until decomposition of the hydrates is complete. Such decomposition is revealed by an increase of pressure in reactor 1 and by the visual disappearance of the opacity of the fluid which is produced by the presence of hydrates. Finally, the temperature is slowly lowered at the rate of 1° C./hour and the temperature is determined at which the hydrates begin to form, then the temperature is determined at which the circuit is totally blocked and where no fluid flow is possible.

The following examples illustrate non limitatively the use of a few additives in the method of the invention for transporting hydrate forming fluids. Examples 1 and 2 are given by way of comparison.

EXAMPLE 1

In this example a fluid is used formed by volume of 20% water and 80% condensate. The ponderal composition of the condensate is for molecules having less than 11 carbon atoms: 20% of paraffins and isoparaffins, 48% of naphthenes, 10% of aromatics; and for molecules having at least 11 carbon atoms 22% of a mixture of paraffins, isoparaffins. naphthenes and aromatics.

The gas used comprises by volume 98% methane and 2% ethane. The experiment is carried out at a pressure of 7 MPa held constant by supplying gas. Under these conditions, the temperature at which hydrates begin to form, at the time of the second lowering of temperature, is 11.4° C. and blockage of the flow is obtained by the growth and coalescence of the hydrates when the temperature reaches +11° C., i.e. 24 minutes after the beginning of formation of the hydrates.

EXAMPLE 2

In this example, the same fluid, the same gas and the same pressure are used as in example 1 but 5% by weight of methanol, with respect to the water of the mixture, is added to the circulating fluid, methanol being the most generally used for transporting oil field effluents when there is a risk of hydrate formation. Under these conditions it is observed that the temperature at which hydrates begin to form is 9.4° C. and that the temperature at which no fluid flow is possible, because of the growth and coalescence of the hydrate is 9° C.

EXAMPLE 3

The operating mode is as for example 1, but 0.25% by weight, with respect to the water, of copra diethanolamides is added to the circulating fluid.

Under these conditions, it can be observed that the temperature at which hydrates begin to form is 7.5° C. and that at −10° C., minimum operating temperature, no blockage of the flow of fluid was observed.

EXAMPLE 4

The operating mode is as for example 3 with 0.25% by weight of copra diethanolamides but when −2° C. is reached, at which temperature there is no blockage, the flow of fluid is stopped and at the end of an hour's stoppage, the pump is brought back into service for two minutes to see if there is a blockage.

Under these conditions, it can be observed that after 24 hours at −2° C. no blockage occurred and that each time the pump is brought back into service, every hour, the flow of fluid containing the hydrates takes place normally.

EXAMPLE 5

The operating mode is as for example 1, but 0.2% by weight, with respect to the water, of colza oil diethanolamides is added to the circulating fluid.

Under these conditions, the temperature at which hydrates begin to form is 8.3° C. and it was observed that at −5° C. no blockage of the flow of fluid occurred.

EXAMPLE 6

The operating mode is as for example 1, but 0.1% by weight, with respect to the water, of butter diethanolamides is added to the circulating fluid.

Under these conditions, the temperature at which hydrates begin to form is 10° C. and it was observed that at 3° C. blockage of the flow of fluid occurred.

EXAMPLE 6

The operating mode is as for example 1, but 0.5% by weight, with respect to the water, of sodium dioctylsulfosuccinate at 65% weight concentration is added to the circulating fluid.

Under these conditions, it was observed that the temperature at which hydrates begin to form is 9.5° C. and that the temperature at which there is blockage of the flow of fluid +7.5° C.

EXAMPLE 8

The operating mode is as for example 1, but 0.2% by weight, with respect to the water, of sorbitan monolaurate is added to the circulating fluid.

Under these conditions, it was observed that the temperature at which hydrates begin to form is 9.7° C. and that blockage of the flow of fluid occurs at a temperature of +5° C.

EXAMPLE 9

The operating mode is as for example but 0.2% by weight, with respect to the water, of a mixture of 80% by weight of sorbitan monolaurate and 20% by weight of sodium dioctylsulfosuccinate at a weight concentration of 65% is added to the circulating fluid.

Under these conditions, it is observed that the temperature at which hydrates begin to form is 9.3° C. and that there is blockage of the flow of fluid at a temperature of 4.5° C.

In examples 1 and 2 in the presence of methanol alone, or with the fluid to be tested alone, blockage of the loop is observed very rapidly after the beginning of formation of the hydrates, i.e. 0.4° C. below the temperature at which hydrates begin to form, namely 24 minutes after reaching this temperature, the time required for coalescence and growth of the hydrates.

On the other hand, in examples 3, 4 and 5, for test temperatures below the temperature at which hydrates begin to form, for examples 6 to 9 between temperatures at which hydrates begin to form and the temperature at which fluid flow is blocked, it is observed that the hydrates form crystals dispersed in the fluid and that these crystals can be transported without blocking the fluid flow.

Examples 7, 8 and 9 shows the synergy produced by the association of an anionic amphiphilic compound (sodium dioctylsulfosuccinate) and a non ionic amphiphilic compound (sorbitan monolaurate) for delaying the formation of hydrates and causing dispersion thereof in the fluid, when they are formed.

Figure 2:
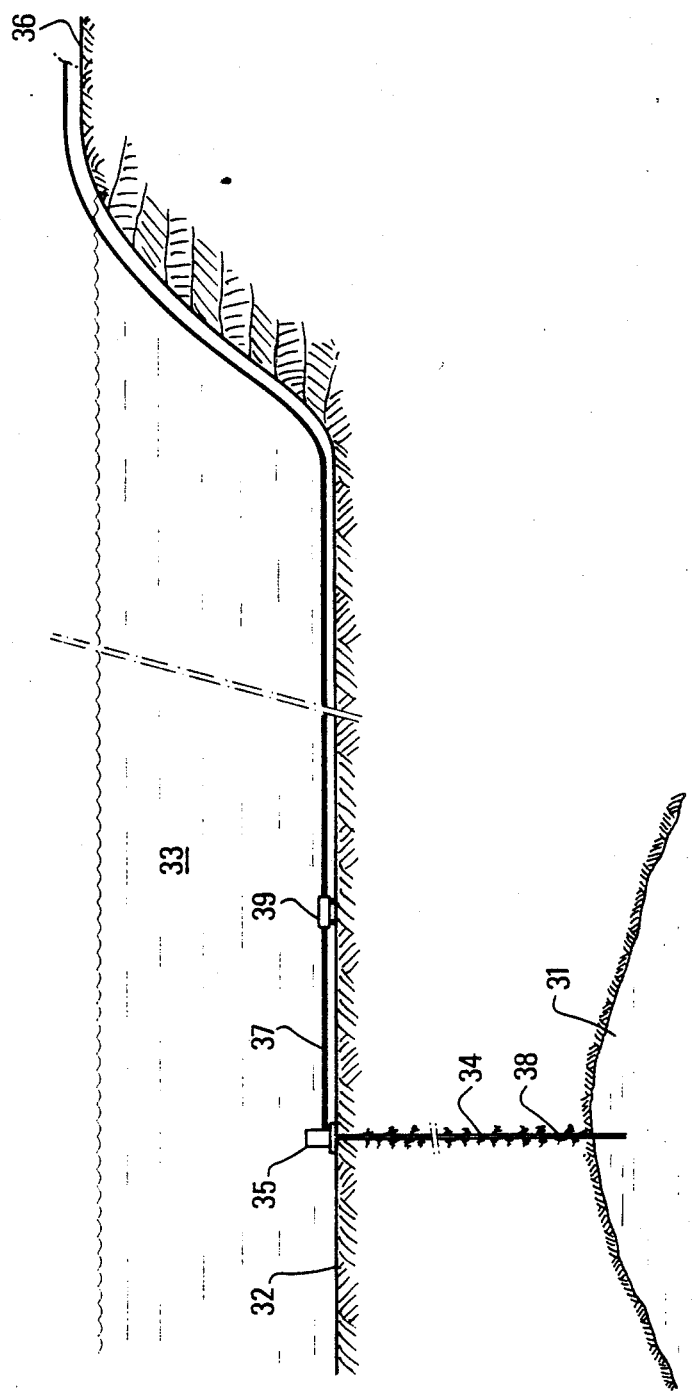
FIG. 2 is a schematic view illustrating the manner in which the transport method of the present invention is applied to the production of hydrate-forming effluents in an underwater petroleum-producing formation.

Applied more particularly to petroleum effluents, the transport method of the invention will be well understood and its advantages will appear clearly from one embodiment illustrated by means of FIG. 2, showing the under-water production and transport of these hydrate forming effluents.

This hydrate forming effluent, which may for example be either a crude oil containing gas and water, or natural gas and water, comes from geological formations 31 disposed under the bed 32 of the sea 33 and worked through a well 34. The upper end of this well 34 or well head 35, which is disposed substantially at the level of the sea bed 32 is connected by a pipe 37 placed on the bottom 32 of the sea to storage or processing installations disposed on emergent land 36. This pipe 37 may be some tens or hundreds of kilometers in length.

When the pressure of the effluent present in the geological formations to be produced is not sufficient, either for extracting the effluent from formations, or for transporting the effluent as far as the emergent land, a well pump 38 and/or a sea bottom pump 39 are placed respectively in well 34 at the required hydraulic height and/or in pipe 37.

Furthermore, since the temperature at the bottom of the sea may reach 3° C., and since the effluent is in thermal contact with the sea through the wall of the pipe, the temperature of the effluent which is initially high when it is in the well finishes at the temperature of the sea and when, on the other hand, the composition of the effluent and the pressure are favorable to hydrate formation, these hydrates agglomerate, form plugs and obstruct the pipe.

To overcome this drawback, the method of the invention proposes:

injecting into the effluent (or the hydrate forming fluid) before or during the formation of such hydrates, an additive adapted for reducing the tendency to agglomeration of the hydrates, so as to obtain one or more hydrates in dispersed form, and transporting the effluent containing this or these hydrates in dispersed form.

Advantageously, as is illustrated in FIG. 2, the additive may be injected upstream of one of the pumps 38 or 39, the furthest upstream possible from the location where the effluent is under conditions where hydrates form.

Agitation may also be provided before or during formation of the hydrates, for increasing the dispersant activity of the additive.

The additive may comprise substituted or non substituted carboxylic acid ethoxylated or non ethoxylated ethanolamides.

The additive may comprise polyol esters and preferably polyol esters comprising at least three hydroxy groups.

The additive may comprise two amphiphilic compounds, the first of these compounds being anionic, such as sodium dioctylsulfosuccinate, the second of these compounds being a non ionic compound such as sorbitan monolaurate.

What is claimed is:

1. A method of transporting in a duct a fluid comprising gas and water, and being under conditions where at least one hydrate is formed, the hydrates being formed from said gas and said water, wherein, before or during the formation of the hydrate or hydrates, an additive is injected into said fluid for reducing the tendency to agglomeration of the hydrate so as to obtain one or more hydrates in dispersed form, and said fluid is transported containing said hydrate or hydrates in dispersed form.

2. The method as claimed in claim 1, in which a pump is placed in said duct, wherein said additive is injected into said fluid upstream of said pump.

3. The method as claimed in claim 1, in which said additive has a certain dispersant activity, wherein agitation is provided for increasing the activity of said additive substantially at the moment when the conditions are present for the formation of one or more hydrates in said fluid.

4. The method as claimed in claim 1, wherein said fluid comprises hydrocarbons including oil, natural gas and said water or petroleum gas.

5. The method as claimed in claim 1, wherein said additive comprises at least one amphiphilic compound.

6. The method as claimed in claim 1, wherein said additive is an ionic amphiphilic compound.

7. The method as claimed in claim 1, wherein said additive is an anionic amphiphilic compound.

8. The method as claimed in claim 7, wherein said additive is a sulfonate.

9. The method as claimed in claim 8, wherein said additive is a sulfosuccinic compound.

10. The method as claimed in claim 1, wherein said additive is a non ionic amphiphilic compound having at least three hydroxy groups.

11. A method of transporting a fluid comprising gas and water in a duct, said fluid being under conditions where at least one hydrate is formed, the at least one hydrate being formed from said gas and said water, wherein, before or during the formation of the at least one hydrate, an additive is injected into said fluid for reducing the tendency of the at least one hydrate to agglomerate so as to obtain at least one hydrate in dispersed form, and said fluid is transported containing said at least on hydrate in dispersed form; said additive comprises at least two amphiphilic compounds, the first of these compounds being an anionic amphiphilic compound, the second of these compounds being a non ionic amphiphilic compound.

12. A method of transporting a fluid comprising gas and water in a duct, said fluid being under conditions in which at least one hydrate is formed from said gas and water, which comprises injecting at least one additive into said fluid before or during formation of the at least one hydrate for reducing the tendency of the at least one hydrate to agglomerate and to obtain the at least one hydrate in a dispersed form within said fluid and transporting the fluid containing said at least one hydrate in dispersed form; said additive comprising at least one amphiphilic compound selected from the group consisting of a non-ionic amphiphilic compound, an anionic amphiphilic compound and a cationic amphiphilic compound.

13. The method as claimed in claim 12, wherein said fluid comprises hydrocarbons including oil, natural gas or petroleum gas and said water.

14. The method as claimed in claim 12, wherein said additive comprises at least two amphiphilic compounds.

* * * * *

US004915176B1

REEXAMINATION CERTIFICATE (3553rd)

United States Patent [19]
Sugier et al.

[11] B1 4,915,176
[45] Certificate Issued Jun. 23, 1998

[54] METHOD OF TRANSPORTING A HYDRATE FORMING FLUID

[75] Inventors: André Sugier; Paul Bourgmayer, both of Rueil Malmaison; Emmanuel Behar, Cergy; Edouard Freund, Rueil Malmaison, all of France

[73] Assignee: Institut Francais du Petrole, Rueil Malmaison, France

Reexamination Request:
No. 90/004,366, Sep. 13, 1996

Reexamination Certificate for:
Patent No.: 4,915,176
Issued: Apr. 10, 1990
Appl. No.: 288,985
Filed: Dec. 23, 1988

[30] Foreign Application Priority Data

Dec. 30, 1987 [FR] France .................. 87 18435

[51] Int. Cl.$^6$ ............. E21B 37/06; E21B 41/02; E21B 43/01; F17D 1/14
[52] U.S. Cl. ............. 166/371; 137/13; 166/902; 507/90; 507/259
[58] Field of Search .............. 166/310, 370, 166/371, 902; 137/13; 507/90, 259

[56] References Cited

U.S. PATENT DOCUMENTS

| | | | |
|---|---|---|---|
| 3,348,614 | 10/1967 | Sinclair et al. | 166/310 |
| 4,132,535 | 1/1979 | Rivers, Jr. et al. | 137/13 X |
| 4,256,282 | 3/1981 | Goldschlid et al. | 166/310 X |
| 4,625,803 | 12/1986 | Walhaug et al. | 166/310 |
| 4,697,426 | 10/1987 | Knowles, Jr. | 166/370 X |
| 4,702,758 | 10/1987 | Geer | 166/370 X |

FOREIGN PATENT DOCUMENTS

| | | | |
|---|---|---|---|
| 612901 | 1/1961 | Canada | 166/310 |
| 644941 | 1/1979 | U.S.S.R. | 166/310 |
| 1275088 | 12/1986 | U.S.S.R. | 166/371 |
| 1314019 | 5/1987 | U.S.S.R. | 166/371 |
| 1339235 | 9/1987 | U.S.S.R. | 166/310 |

OTHER PUBLICATIONS

McCoy, James W., *The Chemical Treatment of Cooling Water*, Chemical Publishing Company, New York, 1974, pp. 66, 67.

Gill, J.S. et al., *Mechanism of Scale Inhibition by Phosphonates*, 1983, pp. 26–32.

*Primary Examiner*—George A. Suchfield

[57] ABSTRACT

A method is provided for transporting in a duct a fluid comprising gas and water, and being under conditions where at least one hydrate is formed, the hydrates being formed from said gas and said water, before or during the formation of the hydrate or hydrates, an additive is injected into said fluid for reducing the tendency to agglomeration of the hydrate so as to obtain one or more hydrates in dispersed form, and said fluid is transported containing said hydrate or hydrates in dispersed form.

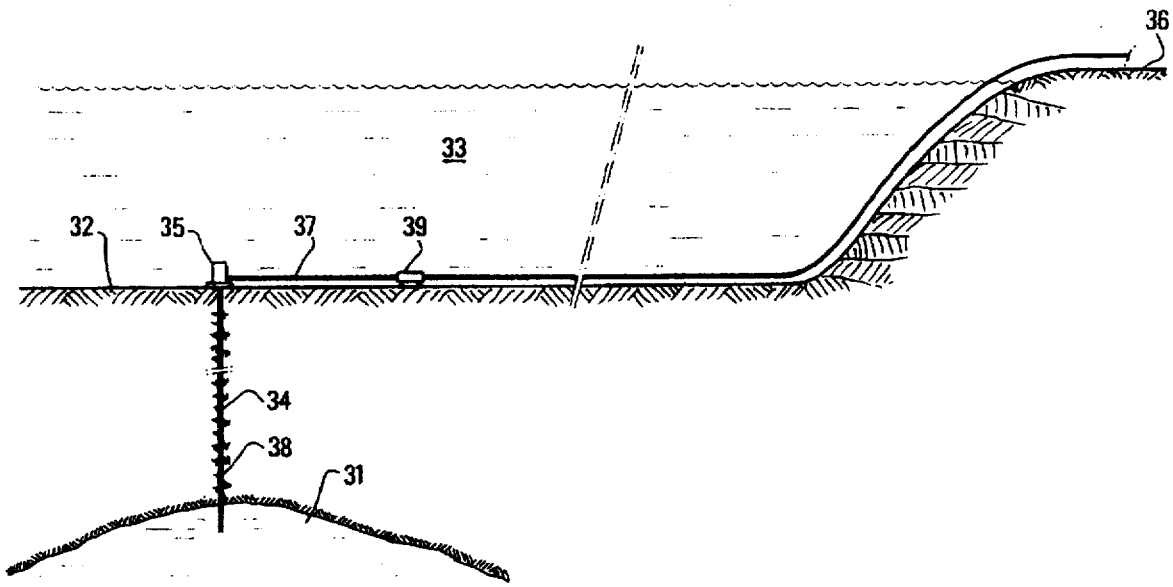

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3, 5, 6, 10, 12 and 13 is confirmed.

Claims 4, 7, 9, 11 and 14 are determined to be patentable as amended.

Claim 8, dependent on an amended claim, is determined to be patentable.

New claims 15–38 are added and determined to be patentable.

4. The method as claimed in claim 1, wherein said fluid comprises hydrocarbons including oil, natural gas *or petroleum gas* and said water [or petroleum gas].

7. [The] *A* method [as claimed in claim 1] *of transporting in a duct a fluid comprising gas and water, and being under conditions where at least one hydrate is formed, the hydrates being formed from said gas and said water, wherein before or during the formation of the hydrate or hydrates, an additive is injected into said fluid for reducing the tendency to agglomeration of the hydrate so as to obtain one or more hydrates in dispersed form, and said fluid is transported containing said hydrate or hydrates in dispersed form, and wherein said additive is an anionic amphiphilic compound selected from the group consisting of a sulfonate and sulfosuccinic compound.*

9. The method as claimed in claim [8] *7*, wherein said additive is a sulfosuccinic compound.

11. A method of transporting a fluid comprising gas and water in a duct, said fluid being under conditions where at least one hydrate is formed, the at least one hydrate being formed from said gas and said water, wherein, before or during the formation of the at least one hydrate, an additive is injected into said fluid for reducing the tendency of the at least one hydrate to agglomerate so as to obtain at least one hydrate in dispersed form, and said fluid is transported containing said at least [on] *one* hydrate in dispersed form; said additive comprises at least two amphiphilic compounds, the first of these compounds being an anionic amphiphilic compound, the second of these compounds being a non ionic amphiphilic compound.

14. [The] *A* method [as claimed in claim 12] *of transporting a fluid comprising gas and water in a duct, said fluid being under conditions in which at least one hydrate is formed from said gas and water, which comprises injecting at least one additive into said fluid before or during formation of the at least one hydrate for reducing the tendency of the at least one hydrate to agglomerate and to obtain the at least one hydrate in a dispersed form within said fluid and transporting the fluid containing said at least one hydrate in dispersed form, wherein said additive comprises at least two amphiphilic compounds.*

*15. The method as claimed in claim 12, wherein said additive comprises at least one non-ionic amphiphilic compound reducing the tendency of the at least one hydrate to agglomerate.*

*16. The method as claimed in claim 12, wherein said additive comprises at lesat one anionic amphiphilic compound reducing the tendency of the at least one hydrate to agglomerate.*

*17. A method of transporting a fluid comprising gas and water in a duct, said fluid being under conditions in which at least one hydrate is formed from said gas and water, which comprises injecting at least one additive into said fluid before or during formation of the at least one hydrate for reducing the tendency of the at least one hydrate to agglomerate and to obtain the at least one hydrate in a dispersed form within said fluid and transporting the fluid containing said at least one hydrate in dispersed form, wherein said additive comprises at least one cationic amphiphilic compound reducing the tendency of the at least one hydrate to agglomerate.*

*18. The method as claimed in claim 17, wherein the at least one cationic amphiphilic compound comprises a quaternary ammonium salt reducing the tendency of the at least one hydrate to agglomerate.*

*19. A method of transporting a fluid comprising gas and water in a duct, said fluid being under conditions in which at least one hydrate is formed from said gas and water, which comprises injecting at least one additive into said fluid before or during formation of the at least one hydrate for reducing the tendency of the at least one hydrate to agglomerate and to obtain the at least one hydrate in a dispersed form within said fluid and transporting the fluid containing said at least one hydrate in dispersed form, wherein said additive comprises at least one non-ionic amphiphilic compound comprising a copra derivative reducing the tendency of the at least one hydrate to agglomerate.*

*20. A method as claimed in claim 19, wherein said copra derivative is copra diethanolamide.*

*21. The method as claimed in claim 19, in which a pump is placed in said duct, wherein said additive is injected into said fluid upstream of said pump.*

*22. The method as claimed in claim 19, in which said additive has a certain dispersant activity, wherein agitation is provided for increasing the activity of said additive substantially at the moment when the conditions are present for the formation of one or more hydrates in said fluid.*

*23. The method as claimed in claim 19, wherein said fluid comprises hydrocarbons including oil, natural gas or petroleum gas and said water.*

*24. The method as claimed in claim 17, in which a pump is placed in said duct, wherein said additive is injected into said fluid upstream of said pump.*

*25. The method as claimed in claim 17, in which said additive has a certain dispersant activity, wherein agitation is provided for increasing the activity of said additive substantially at the moment when the conditions are present for the formation of one or more hydrates in said fluid.*

*26. The method as claimed in claim 17, wherein said fluid comprises hydrocarbons including oil, natural gas or petroleum gas and said water.*

*27. The method as claimed in claim 14, in which a pump is placed in said duct, wherein said additive is injected into said fluid upstream of said pump.*

*28. The method as claimed in claim 14, in which said additive has a certain dispersant activity, wherein agitation is provided for increasing the activity of said additive* substantially at the moment when the conditions are present for the formation of one or more hydrates in said fluid.

29. The method as claimed in claim 14, wherein said fluid comprises hydrocarbons including oil, natural gas or petroleum gas and said water.

30. The method as claimed in claim 12, in which a pump is placed in said duct, wherein said additive is injected into said fluid upstream of said pump.

31. The method as claimed in claim 12, in which said additive has a certain dispersant activity, wherein agitation is provided for increasing the activity of said additive substantially at the moment when the conditions are present for the formation of one or more hydrates in said fluid.

32. The method as claimed in claim 12, wherein said fluid comprises hydrocarbons including oil, natural gas or petroleum gas and said water.

33. The method as claimed in claim 11, in which a pump is placed in said duct, wherein said additive is injected into said fluid upstream of said pump.

34. The method as claimed in claim 11, in which said additive has a certain dispersant activity, wherein agitation is provided for increasing the activity of said additive substantially at the moment when the conditions are present for the formation of one or more hydrates in said fluid.

35. The method as claimed in claim 11, wherein said fluid comprises hydrocarbons including oil, natural gas or petroleum gas and said water.

36. The method as claimed in claim 7, in which a pump is placed in said duct, wherein said additive is injected into said fluid upstream of said pump.

37. The method as claimed in claim 7, in which said additive has a certain dispersant activity, wherein agitation is provided for increasing the activity of said additive substantially at the moment when the conditions are present for the formation of one or more hydrates in said fluid.

38. The method as claimed in claim 7, wherein said fluid comprises hydrocarbons including oil, natural gas or petroleum gas and said water.

* * * * *